(12) United States Patent
Nagasrinivasa et al.

(10) Patent No.: US 11,752,313 B2
(45) Date of Patent: Sep. 12, 2023

(54) BALLOON CATHETER INCLUDING A DRUG DELIVERY SHEATH

(71) Applicant: Medtronic Vascular, Inc., Santa Rosa, CA (US)

(72) Inventors: Shyam Nagasrinivasa, Santa Rosa, CA (US); Claudio Silvestro, Healdsburg, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 395 days.

(21) Appl. No.: 17/167,285

(22) Filed: Feb. 4, 2021

(65) Prior Publication Data

US 2021/0154445 A1      May 27, 2021

Related U.S. Application Data

(62) Division of application No. 15/137,934, filed on Apr. 25, 2016, now Pat. No. 10,940,294.

(51) Int. Cl.
*A61M 25/10*      (2013.01)

(52) U.S. Cl.
CPC .......... *A61M 25/104* (2013.01); *A61M 25/10* (2013.01); *A61M 2025/105* (2013.01);
(Continued)

(58) Field of Classification Search
CPC ................ A61M 25/104; A61M 25/10; A61M 2025/105; A61M 2025/1081;
(Continued)

(56) References Cited

U.S. PATENT DOCUMENTS 5,304,121 A   *   4/1994   Sahatjian ................ A61L 29/16
                                                                                                                    606/194
7,704,545 B2      4/2010   Kantor
(Continued)

FOREIGN PATENT DOCUMENTS

CN        101045175      10/2007
WO      2009005933      1/2009

OTHER PUBLICATIONS

Extended European Search Report for patent application No. EP 17165252.2, dated Sep. 14, 2017; 9 pages.
(Continued)

*Primary Examiner* — Nathan R Price
*Assistant Examiner* — Justin L Zamory
(74) *Attorney, Agent, or Firm* — Mueting Raasch Group

(57) ABSTRACT

A balloon catheter includes an elongated catheter shaft, an expandable balloon connected to the elongated catheter shaft, and a sheath that defines a lumen and includes a therapeutic agent disposed within the lumen. The balloon catheter further includes a first configuration and a second configuration. When in the first configuration, the expandable balloon is disposed distally from the sheath such that an outer surface of the expandable balloon does not contact the lumen. Further, when in the second configuration, at least a portion of the outer surface of the expandable balloon is disposed within the lumen of the sheath such that it contacts the therapeutic agent. At least a portion of the therapeutic agent that contacts the outer surface of the expandable balloon is transferred from the lumen of the sheath to the outer surface of the expandable balloon when the balloon catheter is in the second configuration.

20 Claims, 7 Drawing Sheets

(52) U.S. Cl.
CPC ............... *A61M 2025/1031* (2013.01); *A61M 2025/1081* (2013.01)

(58) Field of Classification Search
CPC .. A61M 2025/0681; A61M 2025/1015; A61M 2025/1031; A61M 2025/1068; A61M 2025/1075; A61M 2025/1084; A61M 2025/1088
See application file for complete search history.

(56) References Cited

U.S. PATENT DOCUMENTS

| | | | |
|---|---|---|---|
| 2003/0233115 A1* | 12/2003 | Eversull | ............ A61M 25/1002 606/194 |
| 2004/0181273 A1 | 9/2004 | Brasington et al. | |
| 2005/0113687 A1* | 5/2005 | Herweck | ............... A61M 25/10 600/435 |
| 2009/0105686 A1 | 4/2009 | Snow et al. | |
| 2010/0228333 A1 | 9/2010 | Drasler et al. | |
| 2011/0054396 A1 | 3/2011 | Kangas et al. | |
| 2011/0301565 A1 | 12/2011 | Weber | |
| 2012/0283636 A1 | 11/2012 | Rizg et al. | |
| 2015/0190618 A1 | 7/2015 | Kantor | |

OTHER PUBLICATIONS

CN Patent Application No. 201710274104.5 filed Apr. 4, 2016; Office Action dated Dec. 3, 2020.

* cited by examiner

BALLOON CATHETER INCLUDING A DRUG DELIVERY SHEATH

RELATED APPLICATIONS

This application is a Division of and claims the benefit of U.S. patent application Ser. No. 15/137,934 filed Apr. 25, 2016, now allowed. The disclosures of which are herein incorporated by reference in their entirety.

FIELD OF INVENTION

The present invention relates to drug coated balloon catheters, and more specifically to a balloon catheter including drug delivery sheath.

BACKGROUND

Blockages in vessels, such as arterial blockages, are traditionally treated using percutaneous transluminal angioplasty (PTA) in which an expandable balloon is used to push open and expand the lumen of a blocked vessel. However, PTA may cause neo-intimal hyperplasia and consequently arterial restenosis, which causes the vessel lumen to again shrink and become at least partially blocked. Recently, the use of drug coated balloons has been developed to provide a minimally invasive procedure to prevent and block arterial restenosis. However, in such a procedure, typically both a traditional PTA balloon catheter and a drug coated balloon catheter are used. For example, a traditional PTA balloon catheter is first used to mechanically pre-dilate a blockage within the vessel by inflating the balloon of the PTA balloon catheter within the blockage. The PTA catheter can then be withdrawn, and a second PTA balloon catheter that includes a therapeutic agent disposed on an outer surface of a balloon of the catheter (i.e., a drug coated balloon) can then be delivered to the treatment site and inflated such that the therapeutic agent is transferred to the previously dilated treatment site.

To avoid the use of two different balloon catheters, one technique utilizes an expandable sheath that is disposed around a balloon of a balloon catheter. A coating that includes a therapeutic agent can be disposed on an outer surface of the expandable sheath. The coated sheath can be delivered to a treatment site within a patient, and the balloon can be expanded within the sheath, thereby causing the sheath to also expand. The outer surface of the expanded sheath that includes the coating contacts an inner surface of a vessel, thereby delivering the therapeutic agent to the patient. However, such a technique may have drawbacks. For example, the balloon may have to be inflated to higher pressures to expand such an expandable sheath. Further, the expandable sheath may not be as compliant and thus may not make good contact with the vessel wall and/or blockage. Furthermore, the sheath may not be made of the same material historically used to manufacture expandable balloons, thus potentially hindering compatibility with the therapeutic agent and ability to deliver the drug to the vessel wall. Furthermore, materials used to manufacture sheaths are typically not as compliant, and balloon-driven expansion might cause a drastic change in the porosity, mechanical properties, or physical properties of the sheaths, thus impacting the sheath's ability to effectively carry and deliver the therapeutic agent.

SUMMARY

In general, the present disclosure provides various embodiments of a balloon catheter that can both pre-dilate the blockage and deliver a therapeutic agent in a single device. The balloon catheter includes a sheath disposed over at least a portion of an elongated catheter shaft of the catheter. The balloon catheter also includes an expandable balloon connected to the elongated catheter shaft. In one or more embodiments, a therapeutic agent is disposed within a lumen of the sheath. In a first configuration, the balloon of the balloon catheter is disposed distal from the sheath such that an outer surface of the expandable balloon is not in contact with the lumen of the sheath. Further, in a second configuration, at least a portion of the outer surface of the expandable balloon is disposed within the lumen of the sheath such that it contacts the therapeutic agent disposed within the lumen of the sheath. In one or more embodiments, at least a portion of the therapeutic agent is transferred from the lumen of the sheath to the outer surface of the expandable balloon when the balloon catheter is in the second configuration.

In general, in one aspect, the present disclosure describes a balloon catheter that includes an elongated catheter shaft having a proximal end and a distal end, where the elongated catheter shaft defines a longitudinal axis extending between the proximal end and the distal end. The balloon catheter further includes an expandable balloon connected to the elongated catheter shaft adjacent the distal end of the elongated catheter shaft, where the expandable balloon includes an outer surface; and a sheath including an inner surface defining a lumen and a therapeutic agent disposed within the lumen of the sheath, where at least a portion of the elongated catheter shaft is disposed within the lumen of the sheath. The balloon catheter further includes a first configuration and a second configuration, where the expandable balloon and the sheath are configured for movement relative to each other along the longitudinal axis of the elongated catheter shaft between the first configuration and the second configuration. When in the first configuration, the expandable balloon is disposed distally from the sheath such that the outer surface of the expandable balloon does not contact the lumen of the sheath. When in the second configuration, at least a portion of the outer surface of the expandable balloon is disposed within the lumen of the sheath such that it contacts the therapeutic agent. Further, at least a portion of the therapeutic agent that contacts the outer surface of the expandable balloon is transferred from the lumen of the sheath to the outer surface of the expandable balloon when the balloon catheter is in the second configuration.

In various embodiments, the sheath includes an elastomeric material.

In various embodiments, the expandable balloon includes a polymeric material.

In various embodiments, the therapeutic agent is disposed on the inner surface of the lumen of the sheath.

In various embodiments, the lumen of the sheath further includes a substrate connected to the inner surface of the sheath, where the substrate includes the therapeutic agent. In certain embodiments, the substrate is selected from the group consisting of a film, a gel, and a matrix.

In various embodiments, the elongated catheter shaft includes an outer surface that is friction-fit with the inner surface of the sheath.

In various embodiments, expansion of the expandable balloon when the balloon catheter is in the second configuration expands the sheath.

In various embodiments, the elongated catheter shaft includes an inflation lumen disposed along the longitudinal axis that is in fluid communication with the expandable balloon.

In various embodiments, the elongated catheter shaft includes a guidewire lumen disposed along the longitudinal axis.

In various embodiments, no therapeutic agent is disposed on the surface of the expandable balloon when the balloon catheter is in the first configuration.

In general, in another aspect, the present disclosure describes a method of delivering a therapeutic agent to a treatment site disposed on an inner surface of a vessel. The method includes advancing an expandable balloon into the vessel with an elongated catheter shaft having a proximal end and a distal end, where the expandable balloon is connected to the elongated catheter shaft adjacent the distal end of the elongated catheter shaft. The method further includes inflating the expandable balloon such that an outer surface of the expandable balloon contacts the treatment site; deflating the expandable balloon; and advancing a sheath into the vessel over the elongated catheter shaft such that a distal end of the sheath is adjacent the expandable balloon, where the sheath includes an inner surface that defines a lumen and a therapeutic agent disposed within the lumen of the sheath. The method further includes positioning at least a portion of the expandable balloon within the sheath such that the outer surface of the expandable balloon contacts the therapeutic agent within the lumen of the sheath, thereby transferring at least a portion of the therapeutic agent from the lumen of the sheath to the outer surface of the expandable balloon; advancing the expandable balloon beyond the distal end of the sheath; and re-inflating the expandable balloon such that the outer surface of the expandable balloon contacts the treatment site.

In various embodiments, the therapeutic agent is disposed on the inner surface of the sheath.

In various embodiments, the lumen of the sheath further includes a substrate connected to the inner surface of the sheath, where the substrate includes the therapeutic agent. In certain embodiments, the substrate is selected from the group consisting of a film, a gel, and a matrix.

In various embodiments, the method further includes withdrawing the sheath from the vessel.

In various embodiments, the method further includes deflating the expandable balloon, and withdrawing the expandable balloon from the vessel.

In various embodiments, positioning the at least a portion of the expandable balloon within the sheath includes moving the sheath relative to the expandable balloon such that the at least a portion of the expandable balloon is disposed within the lumen of the sheath; and inflating the expandable balloon such that the outer surface of the expandable balloon contacts the substrate or inner surface of the sheath. In certain embodiments, the method includes deflating the expandable balloon after transferring the at least a portion of the therapeutic agent from the substrate or inner surface of the sheath to the outer surface of the expandable balloon.

In various embodiments, positioning the at least a portion of the expandable balloon within the sheath includes advancing the sheath over the expandable balloon such that the sheath is between the treatment site and the expandable balloon.

In various embodiments, positioning the at least a portion of the expandable balloon within the sheath includes withdrawing the expandable balloon from the treatment site and into the sheath.

In general, in another aspect, the present disclosure describes a method of delivering a therapeutic agent to a treatment site disposed on an inner surface of a vessel. The method includes advancing an elongated catheter shaft, an expandable balloon, and a sheath into the vessel, where the elongated catheter shaft includes a proximal end and a distal end. The expandable balloon is connected to the elongated catheter shaft adjacent the distal end of the elongated catheter shaft. The sheath includes an inner surface defining a lumen and a therapeutic agent disposed within the lumen of the sheath. Further, at least a portion of the elongated catheter shaft is disposed within the lumen of the sheath and a distal end of the sheath is adjacent the expandable balloon. The method further includes inflating the expandable balloon such that an outer surface of the expandable balloon contacts the treatment site; deflating the expandable balloon; and positioning at least a portion of the expandable balloon within the sheath such that the outer surface of the expandable balloon contacts the therapeutic agent within the lumen of the sheath, thereby transferring at least a portion of the therapeutic agent from the lumen of the sheath to the outer surface of the expandable balloon. The method further includes advancing the expandable balloon beyond the distal end of the sheath, and re-inflating the expandable balloon such that the outer surface of the expandable balloon contacts the treatment site.

In various embodiments, the therapeutic agent is disposed on the inner surface of the sheath.

In various embodiments, the lumen of the sheath further includes a substrate connected to the inner surface of the sheath, where the substrate includes the therapeutic agent.

In various embodiments, the substrate is selected from the group consisting of a film, a gel, and a matrix.

In various embodiments, the method includes withdrawing the sheath from the vessel.

In various embodiments, the method further includes deflating the expandable balloon, and withdrawing the expandable balloon from the vessel.

In various embodiments, positioning the at least a portion of the expandable balloon within the sheath includes moving the sheath relative to the expandable balloon such that the at least a portion of the expandable balloon is disposed within the lumen of the sheath; and inflating the expandable balloon such that the outer surface of the expandable balloon contacts the substrate or inner surface of the sheath. In certain embodiments, the method further includes deflating the expandable balloon after transferring the at least a portion of the therapeutic agent from the substrate or inner surface of the sheath to the outer surface of the expandable balloon.

In various embodiments, positioning the at least a portion of the expandable balloon within the lumen of the sheath includes advancing the sheath over the expandable balloon such that the sheath is between the treatment site and the expandable balloon.

In various embodiments, positioning the at least a portion of the expandable balloon within the lumen of the sheath includes withdrawing the expandable balloon from the treatment site and into sheath.

The disclosure can be implemented to realize one or more of the following advantages. The procedure to treat a blocked, or partially blocked, vessel lumen may be completed using a single device only. Further, release of the drug during delivery of the device through the vasculature can be significantly reduced, thereby subjecting the patient to less drug overall. Also, since less drug is lost during delivery of the device to the treatment site, less drug is needed on the device. Other features and advantages of the invention are apparent from the following description, and from the claims.

All headings provided herein are for the convenience of the reader and should not be used to limit the meaning of any text that follows the heading, unless so specified.

The terms "distal" and "proximal" are used in the disclosure with respect to a position or direction relative to the treating clinician. "Distal" or "distally" is a position distant from our in a direction away from the clinician. "Proximal" and "proximally" is a position near or in a direction toward the clinician. Further, the term "adjacent the distal end of the elongated catheter shaft" means that an element or component is disposed closer to the distal end of the elongated catheter shaft than to the proximal end of the shaft.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
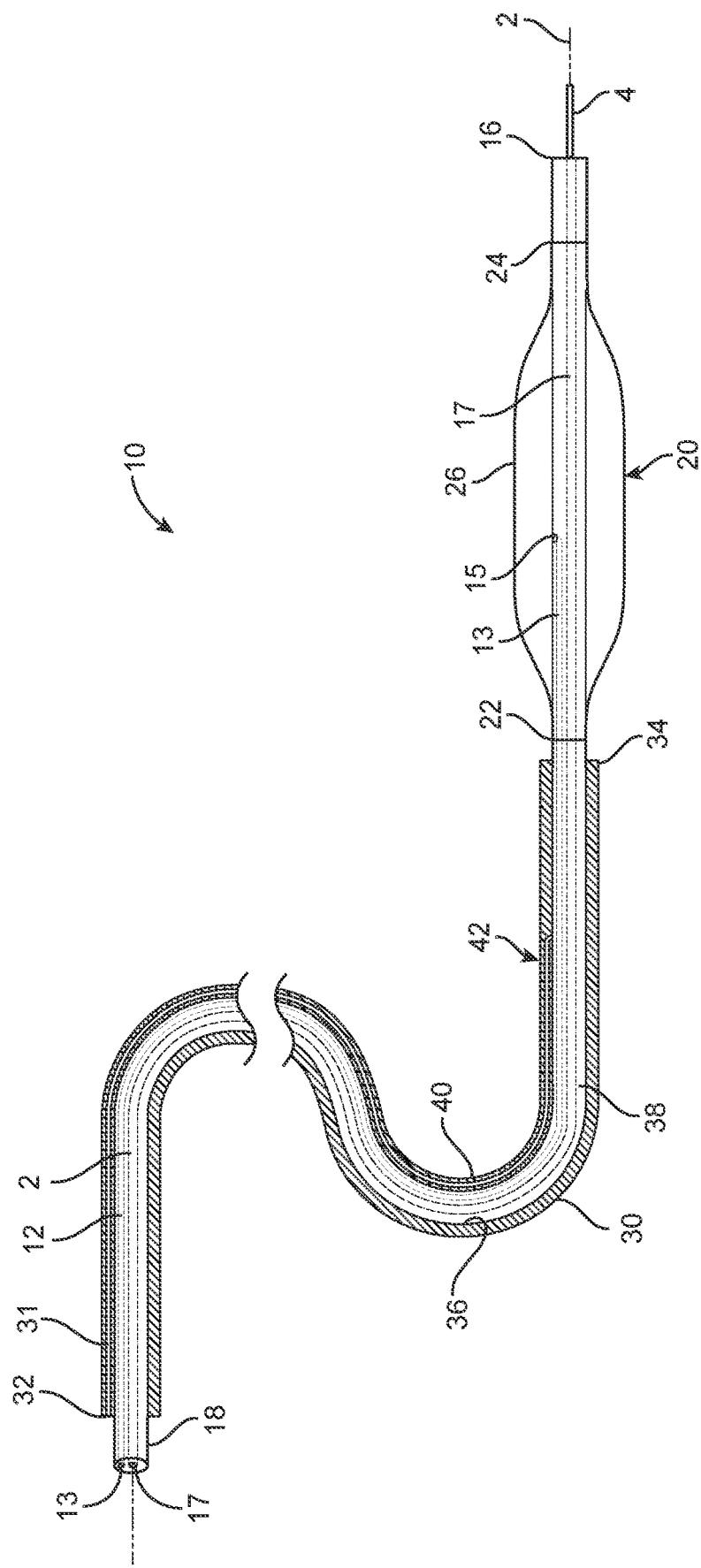
FIG. 1 is a schematic cross-section view of one embodiment of a balloon catheter disposed in a first configuration.

In general, the present disclosure provides various embodiments of a balloon catheter that includes a sheath disposed over at least a portion of an elongated catheter shaft of the catheter. The balloon catheter also includes an expandable balloon connected to the elongated catheter shaft. In one or more embodiments, a therapeutic agent is disposed within a lumen of the sheath. In a first configuration, the balloon of the balloon catheter is disposed distal from the sheath such that an outer surface of the expandable balloon is not in contact with the lumen of the sheath. Further, in a second configuration, at least a portion of the outer surface of the expandable balloon is disposed within the lumen of the sheath such that it contacts the therapeutic agent disposed within the lumen of the sheath. In one or more embodiments, at least a portion of the therapeutic agent is transferred from the lumen of the sheath to the outer surface of the expandable balloon when the balloon catheter is in the second configuration.

One or more embodiments of balloon catheters described herein can provide various advantages over current drug coated balloons. For example, delivery of a therapeutic agent to a treatment site using a drug coated balloon typically requires two separate catheters: a PTA balloon catheter and a drug coated balloon (DCB) catheter. The PTA balloon catheter mechanically pretreats a diseased treatment site by inflation of the balloon against the treatment site. The DCB catheter, which is inserted after removal of the PTA balloon catheter, includes a therapeutic agent disposed on an outer surface of a balloon of the catheter to deliver the therapeutic agent to the treatment site. One or more embodiments of balloon catheters described herein can combine the functionality of the PTA balloon catheter and the DCB balloon catheter into a single device. For example, an exemplary embodiment of a balloon catheter includes a sheath that has an inner surface that defines a lumen, where a therapeutic agent is disposed within the lumen. The sheath can be disposed over at least a portion of an elongated catheter shaft of the balloon catheter. In a first configuration of the catheter, the expandable balloon of the catheter is disposed distally from the sheath such that the outer surface of the expandable balloon does not contact the lumen of the sheath. In this first configuration, the balloon catheter can mechanically treat a treatment site through expansion of the balloon prior to delivery of the therapeutic agent to the treatment site. In a second configuration of the balloon catheter, at least a portion of an outer surface of the expandable balloon can be disposed within the lumen of the sheath such that it contacts the therapeutic agent disposed within the lumen of the sheath. In the second configuration, at least a portion of therapeutic agent can be transferred from the lumen of the sheath to the outer surface of the expandable balloon. The balloon can then be extended beyond the distal end of the sheath and disposed at the treatment site. When so disposed, the balloon of the balloon catheter, which now has the therapeutic agent disposed on its outer surface, can be expanded such that the outer surface of the balloon contacts the treatment site, thereby delivering the therapeutic agent to the treatment site.

In one or more embodiments of balloon catheters described herein, the therapeutic agent can be disposed within the lumen of the sheath either during manufacturing or packaging of the catheter, or in the operating room prior to the catheterization procedure. Placement of the therapeutic agent within the lumen of the sheath instead of on the outer surface of the expandable balloon prior to advancement of the balloon into a vessel of a patient can prevent the therapeutic agent from being diluted or washed out during contact with blood flow within the vessel.

In general, the various embodiments of balloon catheters described herein can be utilized to treat any suitable condition. For example, one or more embodiments of balloon catheters described herein can be utilized to treat, e.g., heart disease, various cardiovascular conditions, and other vascular conditions, including blockages, occlusions, stenoses or diseased regions in the coronary artery, femoral artery, peripheral arteries, and other arteries in the body. Exemplary treatments of vascular conditions can include the prevention or correction of various elements and deficiencies associated with the cardiovascular system, the cerebrovascular system, urine or genital system, biliary conduits, abdominal passageways, and other biological vessels within the body.

FIG. 1-7 are various views of one embodiment of a balloon catheter 10. The balloon catheter 10 includes an elongated catheter shaft 12 having a proximal end 14 and a distal end 16. The elongated catheter shaft 12 defines a longitudinal axis 2 that extends between the proximal end 14 and the distal end 16 of the elongated catheter shaft. The balloon catheter 10 also includes an expandable balloon 20 connected to the elongated catheter shaft 12 adjacent the distal end 16 of the elongated catheter shaft. The expandable balloon 20 includes an outer surface 26.

The catheter 10 also includes a sheath 30 that has an inner surface 36 that defines a lumen 38. In one or more embodiments, a therapeutic agent can be disposed within the lumen 38 of the sheath 30. At least a portion of the elongated catheter shaft 12 is disposed within the lumen 38 of the sheath 30.

Figure 2:
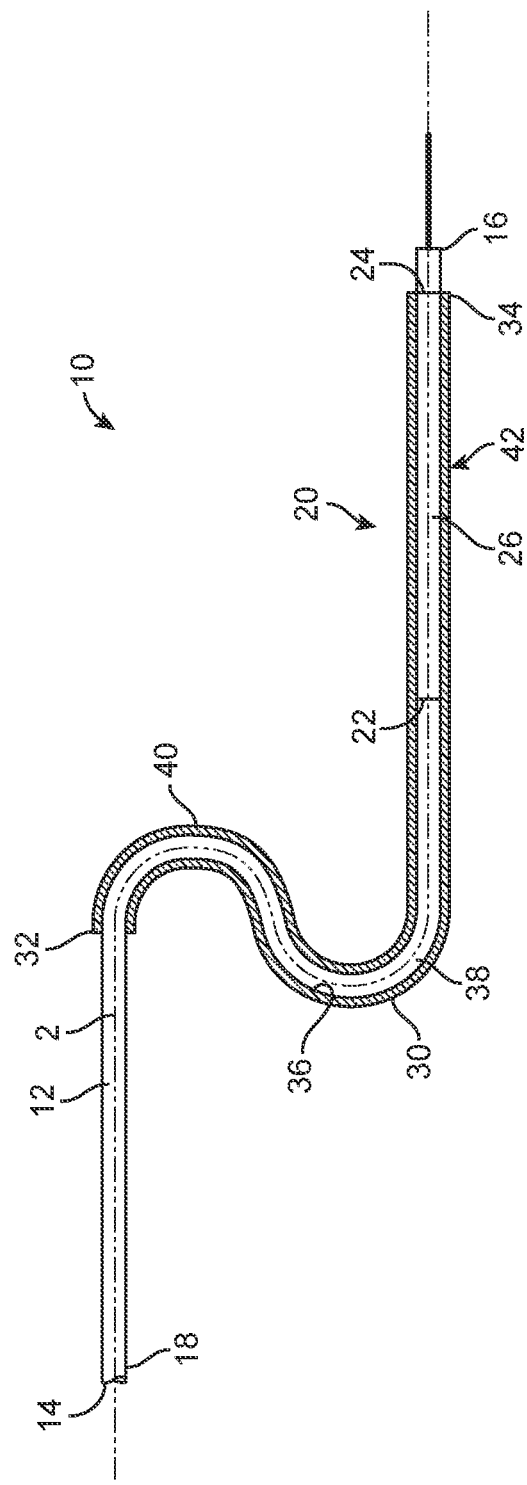
FIG. 2 is a schematic cross-section view of the balloon catheter of FIG. 1 disposed in a second configuration.

The balloon catheter 10 can include a first configuration (as shown in FIG. 1) and a second configuration (as shown in FIG. 2). The expandable balloon 20 and the sheath 30 are configured for movement relative to each other along the longitudinal axis 2 of the elongated catheter shaft 12 between the first configuration and the second configuration. When in the first configuration, the expandable balloon 20 is disposed distally from the sheath 30 such that the outer surface 26 of the expandable balloon does not contact the lumen 38 of the sheath 30 (FIG. 1). Further, when in the second configuration, at least a portion of the outer surface 26 of the expandable balloon 20 is disposed within the lumen 38 of the sheath 30 such that it contacts the therapeutic agent disposed within the lumen 38 (FIG. 2). In one or more embodiments, the entire outer surface 26 of the expandable balloon 20 is disposed within the lumen 38 of the sheath 30 when the balloon catheter 10 is in the second configuration. In one or more embodiments, at least a portion of the therapeutic agent that contacts the outer surface 26 of the expandable balloon 20 is transferred from the lumen 38 of the sheath 30 to the outer surface of the expandable balloon when the balloon catheter 10 is in the second configuration as shown in FIG. 2.

The balloon catheter 10 can include any suitable catheter, e.g., a PTA catheter. Further, the elongated catheter shaft 12 of the balloon catheter 10 can include any suitable material or combination of materials and have any suitable dimensions. In one or more embodiments, the material utilized for the elongated catheter shaft 12 can be selected to not be compatible with or reactive to the therapeutic agent disposed within the lumen 38 of the sheath 30. In such embodiments, transfer of the therapeutic agent from the sheath 30 to the elongated catheter shaft 12 can be prevented or mitigated when the elongated catheter shaft contacts the therapeutic agent. Further, the elongated catheter shaft 12 can take any suitable cross-sectional shape or combination of cross-sectional shapes.

In one or more embodiments, the elongated catheter shaft 12 can include an inflation lumen 13 that is disposed along the longitudinal axis 2 and that is in fluid communication with the expandable balloon 20 through, for example, opening 15 such that the expandable balloon can be inflated and deflated using any suitable technique or combination of techniques via the inflation lumen 13. Further, in one or more embodiments, the elongated catheter shaft 12 can also include a guidewire lumen 17 that is disposed along the longitudinal axis 2. The guidewire lumen 17 of the elongated catheter shaft 12 can be adapted to guide the elongated catheter shaft along a guidewire 4 that can be disposed within a patient such that the expandable balloon 20 can be disposed at a treatment site within the patient.

Connected to the elongated catheter shaft 12 adjacent the distal end 16 of the shaft is the expandable balloon 20. In one or more embodiments, the expandable balloon 20 can include a proximal end 22 and a distal end 24. The proximal end 22 of the expandable balloon 20 can be connected to the elongated catheter shaft 12 adjacent the distal end 16 of the shaft using any suitable technique or combination of techniques. In one or more embodiments, the proximal end 22 of the expandable balloon 20 can be connected to the elongated catheter shaft 12 such that an interior of the expandable balloon 20 is in fluid communication with the inflation lumen 13 disposed within the elongated catheter shaft 12. In such embodiments, the expandable balloon 20 can be inflated and deflated using any suitable device, such as a pump, a syringe, or other inflation device, connected to the inflation lumen 13 of the elongated catheter shaft.

The expandable balloon 20 can include any suitable balloon or combination of balloons for use with balloon catheters. Further, the expandable balloon 20 can include any suitable dimensions and thicknesses. The expandable balloon 20 can include any suitable cross-sectional shape or combination of cross-sectional shapes in a plane that is transverse to the longitudinal axis 2, e.g., round, oval, rectangular, triangular, etc. The expandable balloon 20 can include a cross-sectional shape that remains substantially the same along the longitudinal axis 2. In one or more embodiments, the expandable balloon 20 can include a cross-sectional shape that varies along the longitudinal axis 2, e.g., the expandable balloon includes a tapered portion or portions. While depicted as including a single balloon, the expandable balloon 20 can include two or more balloons that are connected together using any suitable technique or combination of techniques.

Although not shown, the balloon catheter 10 can also include a protective sheath that can be disposed over the expandable balloon. Such protective sheath can protect the expandable balloon as the balloon catheter 10 is being advanced into a patient to the treatment site and then withdrawn over the sheath 30 and elongated catheter shaft 12 to expose the expandable balloon to the treatment site.

Expandable balloon 20 can be compliant, semi-compliant, or noncompliant. Semi-compliant and noncompliant balloons can be utilized for peripheral indications. The expandable balloon can include any suitable material or combination of materials, metallic, polymeric, inorganic, etc. In one or more embodiments, the expandable balloon 20 can include a polymeric material, such as nylon, polyethylene terephthalate, polyethylene, high density polyethylene, polyamide copolymers, polyurethanes, polyvinylchloride, blends, copolymers, and multilayered combinations thereof.

Disposed over at least a portion of the elongated catheter shaft 12 is the sheath 30. The sheath 30 can include any suitable sheath or combination of sheaths. Further, the sheath 30 can be a single unitary sheath or a combination of two or more sheaths that are connected together using any suitable technique or combination of techniques. The sheath 30 includes a proximal end 32 and a distal end 34. The proximal end 32 of the sheath 30 can be disposed adjacent the proximal end 14 of the elongated catheter shaft. Further, the distal end 34 of the sheath 30 can be disposed adjacent the proximal end 22 of the expandable balloon 20 when the balloon catheter 10 is disposed in the first configuration as shown in FIG. 1. The sheath 30 also includes the inner surface 36 and an outer surface 40. The inner surface 36 defines the lumen 38 of the sheath 30.

The sheath 30 can have any suitable dimensions and take any suitable cross-sectional shape or combination of cross-sectional shapes. In one or more embodiments, the sheath 30 can have a length along the longitudinal axis 2 that is less than, greater than, or equal to a length of the elongated catheter shaft 12. Further, the lumen 38 of the sheath 30 can have suitable dimensions and take any suitable cross-sectional shape or combination of cross-sectional shapes. In one or more embodiments, a diameter of the lumen 38 of the sheath 30 can be selected such that the elongated catheter shaft 12 contacts the inner surface 36 of the sheath in one or more regions along the shaft to prevent fluid from entering the lumen when at least a portion of the balloon catheter 10 is disposed within the patient. In one or more embodiments, the elongated catheter shaft 12 includes an outer surface 18 that is friction-fit with the inner surface 36 of the sheath 30. In various embodiments, a distal portion 42 of the lumen 38 of the sheath 30 that will contact the expandable balloon 20 may have a larger diameter than the remainder of the lumen 38 of the sheath 30 that will contact the outer surface 18 of the catheter shaft 12. By having a larger diameter for the distal portion 42 of the lumen 38 that carries the therapeutic agent, the expandable balloon 20 may more easily enter the lumen 38, thereby minimizing the risk of the expandable balloon tearing. Further, the larger diameter in the distal portion 42 of the lumen 38, as compared to the rest of the lumen 38 that contacts the outer surface 18 of the catheter shaft 12, may help prevent the inner surface 36 of the sheath 30 where the therapeutic agent is disposed from touching the catheter shaft 12.

At least a portion of the elongated catheter shaft 12 can be disposed within the lumen 38 of the sheath 30. The sheath 30 can be disposed over the at least a portion of the elongated catheter shaft 12 using any suitable technique or combination of techniques. In one or more embodiments, the proximal end 14 of the elongated catheter shaft 12 can be inserted into the distal end 34 of the sheath 30, and the sheath can be advanced over and along the elongated catheter shaft in a distal direction. In one or more embodiments, the sheath 30 can include a slit that extends the length of the sheath such that the elongated catheter shaft 12 can be inserted into the slit while the sheath 30 is advanced along the elongated catheter shaft 12 in a distal direction.

The sheath 30 can include any suitable material or combination of materials, e.g., metallic, polymeric, inorganic, etc. In one or more embodiments, the sheath 30 can include an elastomeric material. Any suitable elastomeric material or combination of elastomeric materials may be utilized to form the sheath 30, such as, for example, polytetrafluoroethylene, polyimide, polyurethane, polyvinylchloride, shape memory polymers, fiber-reinforced polymers, surface functionalized polymers, blends, copolymers, and multilayered combinations thereof.

In one or more embodiments, one or more therapeutic agents can be disposed within the lumen 38 of the sheath 30. The therapeutic agent can be disposed in any suitable portion or portions of the lumen 38 of the sheath 30. In one or more embodiments, the therapeutic agent is disposed within the lumen 38 of the sheath 30 along the entire length of the sheath. In one or more preferred embodiments, the therapeutic agent is disposed within the lumen 38 of the sheath 30 in the distal portion 42 of the sheath adjacent the distal end 34 of the sheath.

The therapeutic agent can be disposed within the lumen 38 of the sheath 30 using any suitable technique or combination of techniques. Specifically, a suitable technique would include any technique that would enable the therapeutic agent to be released from the sheath 30 when the expandable balloon 20 contacts the inner surface 36 of the sheath 30. Release of the therapeutic agent may be accomplished due to the fact that the expandable balloon 20 was already deployed at the treatment site and will be wet with blood and other fluids. Those fluids in combination with the method by which the therapeutic agent was disposed in the lumen 38 will enable the therapeutic agents to be deposited onto the outer surface 26 of the expandable balloon 20.

Figure 7:
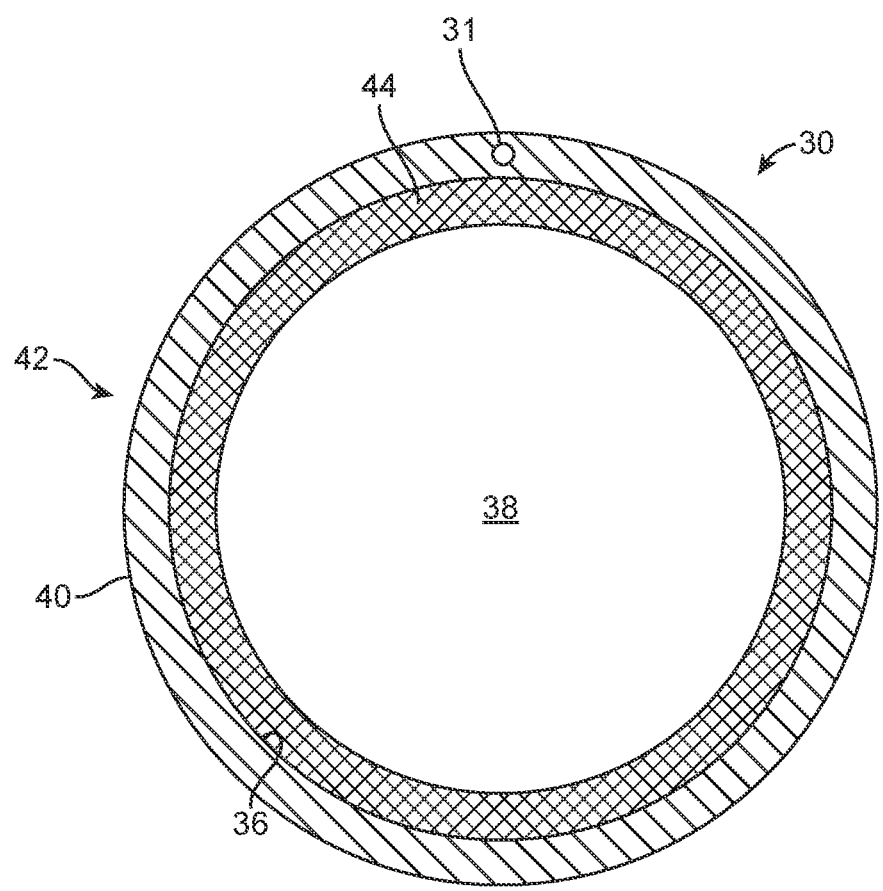
FIG. 7 is a schematic cross-section view of the sheath of the balloon catheter of FIG. 1.

In one or more embodiments, the therapeutic agent may be applied directly to the inner surface 36 of the sheath 30. In one or more other embodiments, the lumen 38 of the sheath 30 can include a substrate that is connected to the inner surface 36 of the sheath, where the substrate includes the therapeutic agent. For example, FIG. 7 is a cross-section view of the distal portion 42 of the sheath 30 of the balloon catheter 10 of FIG. 1. The distal portion 42 of the sheath 30 includes a substrate 44 disposed within the lumen 38 such that the substrate is connected to the inner surface 36 of the sheath. Any suitable technique or combination of techniques can be utilized to connect the substrate 44 to the inner surface 36 of the sheath 30.

The substrate 44 can include any suitable material or combination of materials. In one or more embodiments, the substrate 44 includes a film. The film can include any suitable material or combination of materials, including, for example, multilayer materials, nanomaterials, etc. In one or more embodiments, the substrate includes a gel. The gel can include any suitable material or combination of materials, including for example, hydrogels, biodegradable and bioadsorbable PCL-PEG-PCL hydrogels, thermosensitive hydrogels, Hydroxypropylcellulose (HPC), Hydroxyethyl cellulose (HEC), Xanthan gum, Sodium alginate, Poly (ethylene oxide) and cross-linked homopolymers and copolymers of Acrylic acid. Further, in one or more embodiments, the substrate 44 includes a matrix. The matrix can include any suitable material or combination of materials, including for example, hydroxypropyl methylcellulose (HPMC)-matrices, hydrophobic and hydrophilic matrices, biodegradable matrices, mineral matrices, macro-porous systems.

Further, in one or more embodiments, the distal portion 42 of the sheath 30 can include a material or combination of materials that are different from the material or materials utilized for the remainder of the sheath. The materials of the distal portion 42 of the sheath 30 can include physical or chemical properties that are different from the materials of the remainder of the sheath.

The therapeutic agent can be disposed within the lumen 38 of the sheath 30 using any suitable technique or combination of techniques, e.g., coating, impregnating, etc. For example, the therapeutic agent can be coated onto the substrate 44 or the inner surface 36 of the sheath 30 using, e.g., dipping, spraying, electrostatic coating, painting, or brushing. For example, in an embodiment, a coating solution that includes at least one therapeutic agent and a solvent can be applied to the substrate 44, or directly to the inner surface 36 of the sheath 30, to form a substantially uniform layer of therapeutic agent. The concentration of the therapeutic agent applied to the substrate 44 or the inner surface 36 can vary depending upon the therapeutic agent being used. For example, the therapeutic agent can be mixed in a solution with a solvent and then used to coat the inner surface of the sheath, letting the solvent in excess to evaporate. The therapeutic agent can be also associated to a drug-delivery facilitating molecule (excipient) such as urea or equivalent substances.

In one or more embodiments, after transfer of the therapeutic agent to the outer surface 26 of the expandable balloon 20 when the balloon is in the second configuration, the sheath 30 can be retracted from the body of the patient, and additional therapeutic agent can be reloaded within the lumen 38 of the sheath using any suitable technique or combination of techniques. The sheath 30 can then be advanced over the elongated catheter shaft 12 in a distal direction and into the body of the patient to provide additional therapeutic agent to the expandable balloon using the techniques described herein.

Further, in one or more embodiments, the sheath 30 can include a delivery lumen 31 (FIGS. 1 and 7) that is in fluid communication with the distal portion 42 of the sheath 30. Such delivery lumen 31 can be utilized to deliver the therapeutic agent to the distal portion 42 of the sheath using any suitable technique or combination of techniques. In such embodiments, the distal portion 42 of the sheath 30 may or may not have a therapeutic agent preloaded as described herein. In certain embodiments, the delivery lumen 31 can be used to deliver additional therapeutic agent to the expandable balloon 20 after the therapeutic agent disposed at the distal portion 42 has been used. In other embodiments, no therapeutic agent is disposed at the distal portion, but instead is delivered solely by the delivery lumen 31.

Any suitable therapeutic agent or combination of agents can be utilized with the balloon catheter 10 depending upon the type of treatment that will be delivered to the treatment site within the patient. In general, a therapeutic agent is a composition that is capable of producing a beneficial effect against one or more conditions, including coronary restenosis, cardiovascular restenosis, angiographic restenosis, arterial sclerosis, hyperplasia, and other diseases or conditions. For example, a therapeutic agent can be selected to inhibit or prevent vascular restenosis, a condition corresponding to a narrowing or constriction of the diameter of the bodily lumen where a stent can be placed. An anti-restenosis drug such as rapamycin, a rapamycin analog, or a rapamycin derivative may be used to prevent or reduce the recurrence of narrowing and blockage of the bodily vessel. In one or more embodiments, the antirestenosis drug paclitaxel can be utilized. In one or more embodiments, the therapeutic agent may include an anti-restenosis drug and an excipient. In some preferred embodiments, the anti-restenosis drug and an excipient are paclitaxel and urea.

In one or more embodiments, the therapeutic agent can include an anticancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, a recombinant DNA product, a recombinant RNA product, and anti-sense compound, a collagen, a collagen derivative, a protein, a protein analog, a saccharide, a saccharide derivative, a bioactive agent, other pharmaceutical drugs, or a combination thereof.

The amount of therapeutic agent disposed within the lumen 38 of the sheath 30 can vary depending upon the characteristics of the particular agent, the length of time the expandable balloon 20 will be in place at the treatment site, and other factors. In general, the dose of therapeutic agent disposed within the lumen 38 of the sheath 30 can range from nanograms to milligrams. In one or more embodiments, the therapeutic agent can be coated to achieve a total amount disposed within the lumen 38 of the sheath 30 of at least 1 microgram per square millimeter ($\mu g/mm^2$). In one or more embodiments, the amount of therapeutic agent disposed within the lumen 38 of the sheath 30 can be up to 100 $\mu g/mm^2$. In one or more embodiments, the therapeutic agent can be disposed within the lumen 38 such that a total amount disposed on the surface 26 of the expandable balloon 20 when the balloon catheter 10 is in the second configuration is at least about 1 $\mu g/mm^2$ and no greater than 5 $\mu g/mm^2$.

In one or more embodiments, the therapeutic agent may be disposed within the lumen 38 of the sheath 30 with or without the use of any binding agents, e.g., polymeric binders. Any suitable binding agent or combination of binding agents can be utilized, e.g., ureas, azides, gels, biodegradable/bioabsorbable polymers, etc.

As mentioned herein, the balloon catheter 10 includes the first configuration (as shown in FIG. 1) and the second configuration (as shown in FIG. 2). In general, the expandable balloon 20 and the sheath 30 are configured for movement relative to each other along the longitudinal axis 2 of the elongated catheter shaft 12 between the first configuration and the second configuration. Any suitable technique or combination of techniques can be utilized to manipulate the balloon catheter 10 between the first configuration and the second configuration. In one or more embodiments, the sheath 30 can be advanced over the elongated catheter shaft 12 in a distal direction when the balloon catheter 10 is in the first configuration until at least a portion of the outer surface 26 of the expandable balloon 20 is disposed within the lumen 38 of the sheath. In one or more embodiments, the elongated catheter shaft 12 can be retracted within the sheath 30 in a proximal direction when the balloon catheter 10 is in the first configuration such that at least a portion of the outer surface 26 of the expandable balloon 20 is disposed within the lumen 38 of the sheath 30.

Any suitable technique or combination of techniques can be utilized with the balloon catheter 10 to deliver the therapeutic agent to the treatment site. For example, FIGS. 3-6 illustrate one embodiment of a method of delivering the therapeutic agent to a treatment site 54 that is disposed on an inner surface 52 of a vessel 50. Although described in reference to balloon catheter 10 of FIGS. 1-2 and 7, any suitable balloon catheter can be utilized with the method of FIGS. 3-6.

Figure 3:
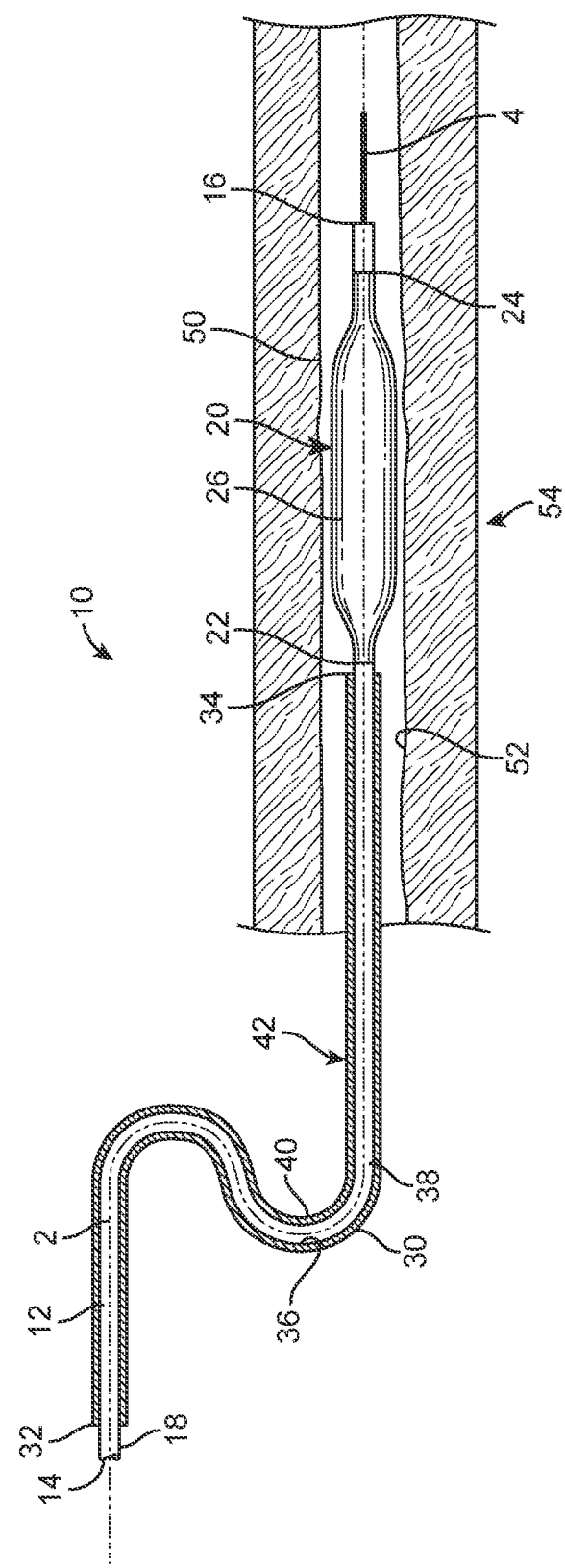
FIG. 3 is a schematic cross-section view of the balloon catheter of FIG. 1 disposed within a patient such that a balloon of the balloon catheter is located at a treatment site.

As shown in FIG. 3, the expandable balloon 20 is advanced into the vessel utilizing the elongated catheter shaft 12. Any suitable technique or combination of techniques as known in the art can be utilized to advance the expandable balloon 20 into the vessel 50 until it reaches the treatment site 54. For example, in one or more embodiments, the balloon catheter 10 can be threaded over the guidewire 4 until the expandable balloon 20 is disposed at the treatment site 54. The balloon catheter 10 as shown in FIG. 3 is in the first configuration. When in the first configuration, the expandable balloon 20 is disposed distally from the sheath 30 such that the outer surface 26 of the expandable balloon does not contact the lumen 38 of the sheath 30. In one or more embodiments, the balloon catheter 10 is advanced to the treatment site 54 with the catheter in the first configuration such that the expandable balloon 20 is disposed at the treatment site 54 prior to any portion of the expandable balloon being disposed within the lumen 38 of the sheath 30. In one or more embodiments, no therapeutic agent is disposed on the surface 26 of the expandable balloon 20 when the balloon catheter 10 is in the first configuration.

Figure 4:
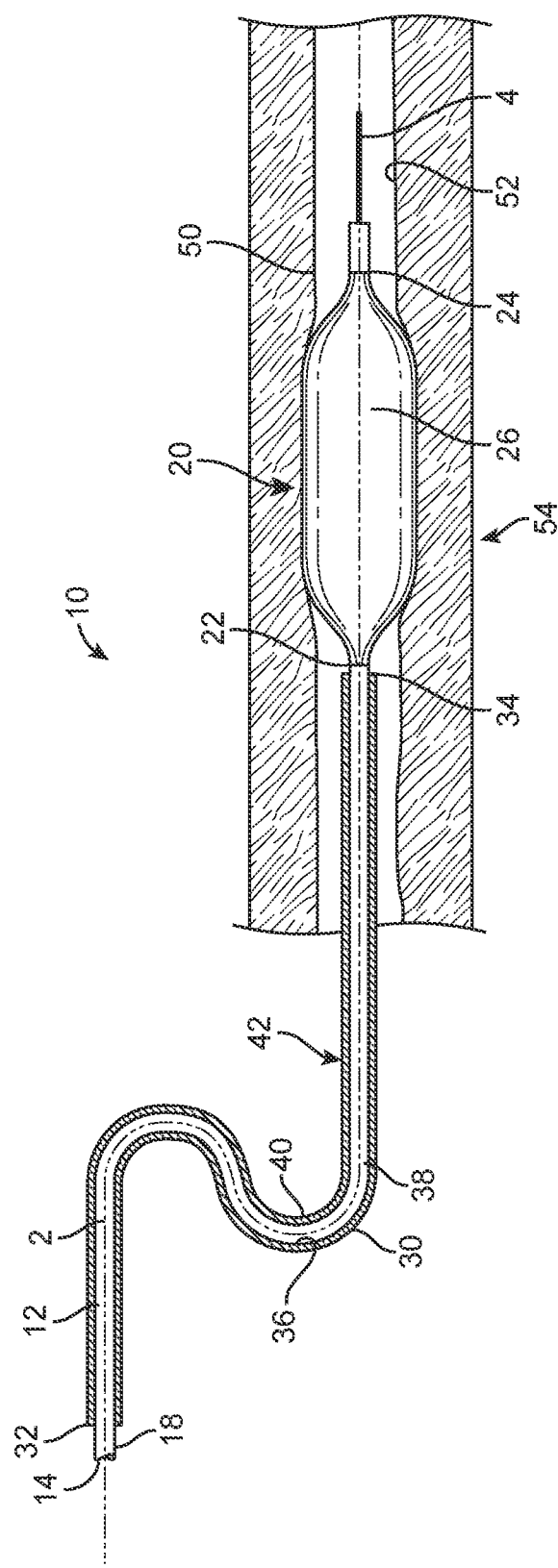
FIG. 4 is a schematic cross-section view of the balloon catheter of FIG. 3 with the balloon of the balloon catheter disposed in an inflated state.

As shown in FIG. 4, the expandable balloon 20 can be inflated such that the outer surface 26 of the expandable balloon 20 contacts the treatment site 54. Any suitable technique or combination of techniques can be utilized to inflate the expandable balloon 20. In one or more embodiments, inflation of the expandable balloon 20 at the treatment site 54 can mechanically treat the treatment site prior to application of a therapeutic agent to the site. In one or more embodiments, the balloon catheter 10 has remained in the first configuration as the expandable balloon 20 is inflated to provide mechanical treatment to the treatment site 54. Following this treatment, expandable balloon 20 can be deflated using any suitable technique or combination of techniques.

Figure 5:
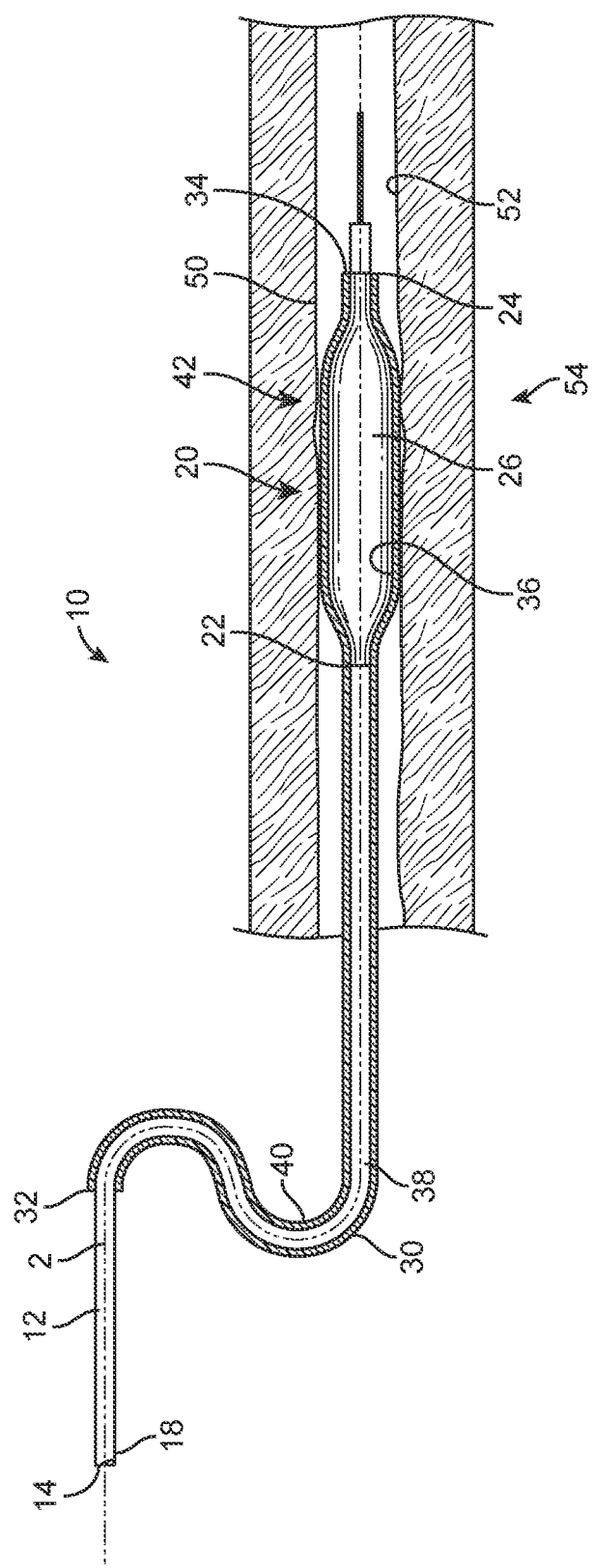
FIG. 5 is a schematic cross-section view of the balloon catheter of FIG. 3 with the balloon of the balloon catheter disposed in the second configuration.

As illustrated in FIG. 5, the sheath 30 can be advanced into the vessel 50 over the elongated catheter shaft 12 such that the distal end 34 of the sheath is adjacent the distal end 16 of the catheter shaft 12 and the expandable balloon 20 is within the lumen 38 of the sheath 30. In one or more embodiments, both the elongated catheter shaft 12 and the expandable balloon 20, along with the sheath 30, can be initially advanced into the vessel 50 of the patient such that both the sheath and the expandable balloon are disposed at or adjacent the treatment site 54. In one or more embodiments, the elongated catheter shaft 12 and the expandable balloon 20 can first be advanced into the vessel 50 and to the treatment site 54 prior to the sheath 30 being disposed over the elongated catheter shaft 12. In other words, the elongated catheter shaft 12 can advance the expandable balloon 20 to the treatment site 54 without the sheath 30 being inserted into the patient or disposed over the elongated catheter shaft 12. In such embodiments, the sheath 30 can be disposed over or slid along the elongated catheter shaft 12 once the expandable balloon 20 is disposed at the treatment site 54.

As shown in FIG. 5, the expandable balloon 20 is at least partially deflated, and at least a portion of the expandable balloon 20 can be disposed within the sheath 30 such that the outer surface 26 of the expandable balloon 20 contacts the therapeutic agent within the lumen 38 of the sheath 30, thereby transferring at least a portion of the therapeutic agent from the lumen 38 of the sheath 30 to the outer surface 26 of the expandable balloon 20. Any suitable technique or combination of techniques can be utilized to dispose the at least a portion of the expandable balloon 20 within the sheath 30. In one or more embodiments, the sheath 30 can be moved along the longitudinal axis 2 of the catheter shaft 12 relative to the expandable balloon 20 such that at least a portion of the expandable balloon 20 is disposed within the lumen 38 of the sheath 30. In one or more embodiments, the sheath 30 can be advanced over the at least a portion of the expandable balloon 20 such that the sheath is between the treatment site 54 and the expandable balloon, e.g., the sheath can be advanced in a distal direction while the expandable balloon remains in place. In one or more embodiments, the expandable balloon 20 can be withdrawn or retracted from the treatment site 54 and into the sheath 30, e.g., the expandable balloon 20 can be withdrawn in a proximal direction while the sheath remains in place. In one or more embodiments, the sheath 30 can be advanced in a distal direction while the expandable balloon 20 is withdrawn in a proximal direction until the at least a portion of the expandable balloon 20 is disposed within the sheath 30. In one or more embodiments, the entire expandable balloon 20 is disposed within the lumen 38 of the sheath 30.

Any suitable technique or combination of techniques can be utilized to transfer the therapeutic agent from the lumen 38 of the sheath 30 to the outer surface 26 of the balloon 20. In one or more embodiments, the expandable balloon 20 can be at least partially re-inflated such that the outer surface 26 of the expandable balloon contacts the substrate 44 or the inner surface 36 of the sheath 30 to ensure increased contact between the outer surface 26 of the balloon 20 and the therapeutic agent disposed within the lumen 38. In one or more embodiments, inflation of the expandable balloon 20 when the balloon catheter 10 is in the second configuration can cause an expansion of a portion or portions of the sheath 30.

In one or more embodiments, the expandable balloon 20 can be rotated within the sheath 30 when the balloon catheter 10 is in the second configuration either with the balloon 20 at least partially inflated or deflated to promote transfer of the therapeutic agent to the outer surface 26 of the balloon 20. In one or more embodiments, the transfer of therapeutic agent to the outer surface 26 of the expandable balloon 20 can also be promoted through the selection of the porosity and/or permeability of the sheath 30 that contacts the outer surface 26 of the balloon 20 and/or the material of the balloon 20. For example, in one or more embodiments, the material utilized to form the distal portion 42 of the sheath 30 can be temperature dependent, and contact with blood of the patient or the proximity to the temperature of the human body can promote transfer of the therapeutic agent onto the balloon surface 26. Further, in one or more embodiments, the blood and other fluids on the outer surface 26 of the expandable balloon 20 will help dislodge the therapeutic agent from the lumen 38 of the sheath 30. In one or more embodiments, the film, gel or matrix described above may at least partially dislodge from the inner surface 36 of the lumen 38 and wrap around the expandable balloon 20.

Figure 6:
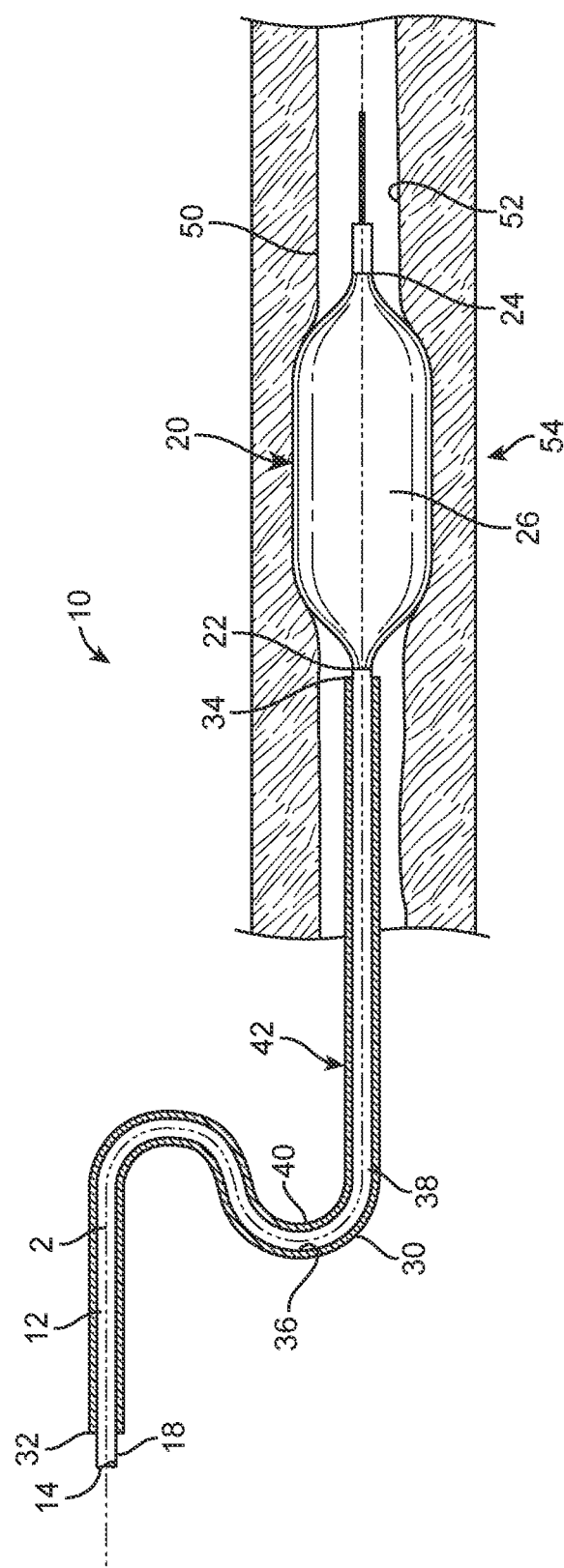
FIG. 6 is a schematic cross-section view of the balloon catheter of FIG. 3 with the catheter having been extended beyond the distal end of the sheath and in an expanded state.

Following transfer of the therapeutic agent from the sheath 30 to the expandable balloon 20, the balloon 20 can be deflated (if the balloon had been inflated while the balloon catheter was in the second configuration) and advanced beyond the distal end 34 of the sheath as shown in FIG. 6. Any suitable technique or combination of techniques can be utilized to advance the expandable balloon 20 beyond the distal end 34 of the sheath 30. In one or more embodiments, the sheath 30 can be withdrawn along the elongated shaft 12 in a proximal direction to expose the outer surface 26 of the balloon to the treatment site 54. In one or more embodiments, the expandable balloon 20 can be advanced beyond the distal end 34 of the sheath 30 by advancing the elongated catheter shaft 12 through the sheath 30 in a distal direction until the balloon 20 is disposed distal from the distal end 34 of the sheath 30.

In one or more embodiments, the balloon catheter 10 as shown in FIG. 6 is in a third configuration. In one or more embodiments, the third configuration is different from the first configuration as the at least a portion of the outer surface 26 of the expandable balloon 20 has been disposed within the lumen 38 of the sheath 30 prior to the catheter 10 being disposed in the third configuration, and thus has therapeutic agent disposed on the outer surface 26 of the expandable balloon 20. In one or more embodiments, no portion of the outer surface 26 of the expandable balloon 20 is disposed within the lumen 38 of the sheath 30 prior to the catheter 10 being disposed in the first configuration, while at least a portion of the outer surface of the expandable balloon is disposed within the lumen prior to the catheter being disposed in the third configuration.

Once the expandable balloon 20 is advanced beyond the distal end 34 of the sheath 30, the balloon 20 can be re-inflated using any suitable technique or combination of techniques such that the outer surface 26 of the balloon 20 contacts the treatment site 54. Inflation of the expandable balloon 20 such that it contacts the treatment site 54 transfers at least a portion of the therapeutic agent from the outer surface 26 of the balloon 20 to the treatment site 54.

After a desired period of time, the expandable balloon 20 can be deflated and withdrawn from the vessel 50 using any suitable technique or combination of techniques. In one or more embodiments, the sheath 30 can first be withdrawn from the vessel 50 using any suitable technique or combination of techniques. In one or more embodiments, the expandable balloon 20 can be withdrawn from the vessel 50 through the sheath 30 while the sheath remains in place. In one or more embodiments, both the expandable balloon 20 and the sheath 30 can be withdrawn simultaneously.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A method of delivering a therapeutic agent to a treatment site disposed on an inner surface of a vessel, comprising:
    advancing an expandable balloon into the vessel with an elongated catheter shaft comprising a proximal end and a distal end, wherein the expandable balloon is connected to the elongated catheter shaft adjacent the distal end of the elongated catheter shaft;
    inflating the expandable balloon such that an outer surface of the expandable balloon contacts the treatment site;
    deflating the expandable balloon;
    advancing a sheath into the vessel over the elongated catheter shaft such that a distal end of the sheath is adjacent the expandable balloon, wherein the sheath comprises an inner surface that defines a lumen and a therapeutic agent disposed within the lumen of the sheath;
    positioning at least a portion of the expandable balloon within the sheath such that the outer surface of the expandable balloon contacts the therapeutic agent within the lumen of the sheath, thereby transferring at least a portion of the therapeutic agent from the lumen of the sheath to the outer surface of the expandable balloon;
    advancing the expandable balloon beyond the distal end of the sheath; and
    re-inflating the expandable balloon such that the outer surface of the expandable balloon contacts the treatment site.

2. The method of claim 1, wherein the therapeutic agent is disposed on the inner surface of the sheath.

3. The method of claim 1, wherein the lumen of the sheath further comprises a substrate connected to the inner surface of the sheath, the substrate comprising the therapeutic agent.

4. The method of claim 3, wherein the substrate is selected from the group consisting of a film, a gel, and a matrix.

5. The method of claim 1, further comprising withdrawing the sheath from the vessel.

6. The method of claim 1, further comprising:
    deflating the expandable balloon; and
    withdrawing the expandable balloon from the vessel.

7. The method of claim 1, wherein positioning the at least a portion of the expandable balloon within the sheath comprises:
    moving the sheath relative to the expandable balloon such that the at least a portion of the expandable balloon is disposed within the lumen of the sheath; and
    inflating the expandable balloon such that the outer surface of the expandable balloon contacts the substrate or inner surface of the sheath.

8. The method of claim 7, further comprising deflating the expandable balloon after transferring the at least a portion of the therapeutic agent from the substrate or inner surface of the sheath to the outer surface of the expandable balloon.

9. The method of claim 1, wherein positioning the at least a portion of the expandable balloon within the sheath comprises advancing the sheath over the expandable balloon such that the sheath is between the treatment site and the expandable balloon.

10. The method of claim 1, to wherein positioning the at least a portion of the expandable balloon within the sheath comprises withdrawing the expandable balloon from the treatment site and into the sheath.

11. A method of delivering a therapeutic agent to a treatment site disposed on an inner surface of a vessel, comprising:
    advancing an elongated catheter shaft, an expandable balloon, and a sheath into the vessel, wherein the elongated catheter shaft comprises a proximal end and a distal end, wherein the expandable balloon is connected to the elongated catheter shaft adjacent the distal end of the elongated catheter shaft, wherein the sheath comprises an inner surface defining a lumen and a therapeutic agent disposed within the lumen of the sheath, and wherein at least a portion of the elongated catheter shaft is disposed within the lumen of the sheath and a distal end of the sheath is adjacent the expandable balloon;
    inflating the expandable balloon such that an outer surface of the expandable balloon contacts the treatment site;
    deflating the expandable balloon;
    positioning at least a portion of the expandable balloon within the sheath such that the outer surface of the expandable balloon contacts the therapeutic agent within the lumen of the sheath, thereby transferring at least a portion of the therapeutic agent from the lumen of the sheath to the outer surface of the expandable balloon;
    advancing the expandable balloon beyond the distal end of the sheath; and
    re-inflating the expandable balloon such that the outer surface of the expandable balloon contacts the treatment site.

12. The method of claim 11, wherein the therapeutic agent is disposed on the inner surface of the sheath.

13. The method of claim 11, wherein the lumen of the sheath further comprises a substrate connected to the inner surface of the sheath, the substrate comprising the therapeutic agent.

14. The method of claim 13, wherein the substrate is selected from the group consisting of a film, a gel, and a matrix.

15. The method of claim 11, further comprising withdrawing the sheath from the vessel.

16. The method of claim 11, further comprising:
    deflating the expandable balloon; and
    withdrawing the expandable balloon from the vessel.

17. The method of claim 11, wherein positioning the at least a portion of the expandable balloon within the sheath comprises:
    moving the sheath relative to the expandable balloon such that the at least a portion of the expandable balloon is disposed within the lumen of the sheath; and
    inflating the expandable balloon such that the outer surface of the expandable balloon contacts the substrate or inner surface of the sheath.

18. The method of claim 17, further comprising deflating the expandable balloon after transferring the at least a portion of the therapeutic agent from the substrate or inner surface of the sheath to the outer surface of the expandable balloon.

19. The method of claim 11, wherein positioning the at least a portion of the expandable balloon within the lumen of the sheath comprises advancing the sheath over the expandable balloon such that the sheath is between the treatment site and the expandable balloon.

20. The method of claim 11, wherein positioning the at least a portion of the expandable balloon within the lumen of the sheath comprises withdrawing the expandable balloon from the treatment site and into sheath.

\* \* \* \* \*